(12) United States Patent
Patek et al.

(10) Patent No.: US 12,057,233 B2
(45) Date of Patent: Aug. 6, 2024

(54) METHOD, SYSTEM, AND COMPUTER READABLE MEDIUM FOR VIRTUALIZATION OF A CONTINUOUS GLUCOSE MONITORING TRACE

(71) Applicant: UNIVERSITY OF VIRGINIA PATENT FOUNDATION, Charlottesville, VA (US)

(72) Inventors: Stephen D. Patek, Charlottesville, VA (US); Marc D. Breton, Charlottesville, VA (US)

(73) Assignee: UNIVERSITY OF VIRGINIA PATENT FOUNDATION, Charlottesville, VA (US)

(*) Notice: Subject to any disclaimer, the term of this patent is extended or adjusted under 35 U.S.C. 154(b) by 0 days.

(21) Appl. No.: 17/696,466

(22) Filed: Mar. 16, 2022

(65) Prior Publication Data

US 2022/0208388 A1 Jun. 30, 2022

Related U.S. Application Data

(63) Continuation of application No. 16/073,920, filed as application No. PCT/US2017/015616 on Jan. 30, 2017, now Pat. No. 11,309,088.

(60) Provisional application No. 62/288,468, filed on Jan. 29, 2016.

(51) Int. Cl.
*G16H 50/50* (2018.01)
*G16H 10/60* (2018.01)
*G16H 40/63* (2018.01)
*G16H 50/70* (2018.01)

(52) U.S. Cl.
CPC ............. *G16H 50/50* (2018.01); *G16H 10/60* (2018.01); *G16H 40/63* (2018.01); *G16H 50/70* (2018.01)

(58) Field of Classification Search
CPC ........ G16H 50/50; G16H 10/60; G16H 50/70; G16H 40/63
USPC ............................................................ 705/2
See application file for complete search history.

(56) References Cited

U.S. PATENT DOCUMENTS

| | | | |
|---|---|---|---|
| 8,818,782 B2 | 8/2014 | Thukral et al. | |
| 11,000,215 B1* | 5/2021 | Simpson | A61B 5/157 |
| 11,309,088 B2* | 4/2022 | Patek | G16H 50/70 |
| 11,376,362 B2* | 7/2022 | Mazlish | G16H 50/20 |
| 2005/0272640 A1 | 12/2005 | Doyle et al. | |
| 2007/0110672 A1 | 5/2007 | Bellott et al. | |
| 2009/0054737 A1 | 2/2009 | Magar et al. | |

(Continued)

OTHER PUBLICATIONS

Office Action (Summons to attend oral proceedings) issued on Sep. 12, 2022, by the European Patent Office in corresponding European Patent Application No. 17 706 022.5. (8 pages).

(Continued)

*Primary Examiner* — Peter H Choi
*Assistant Examiner* — Rachael Sojin Stone
(74) *Attorney, Agent, or Firm* — Buchanan Ingersoll & Rooney PC (57) ABSTRACT

A method and system use mathematical models and available patient information to virtualize a continuous glucose monitoring trace for a period of time. Such a method and system can generate the virtualized trace when episodic patient data is incomplete. Such a method and system can also rely on self-monitored blood glucose measurement information to improve the virtualized continuous glucose monitoring trace.

12 Claims, 8 Drawing Sheets

(56) References Cited

U.S. PATENT DOCUMENTS

| | | |
|---|---|---|
| 2010/0262434 A1 | 10/2010 | Shaya |
| 2011/0047108 A1 | 2/2011 | Chakrabarty et al. |
| 2011/0098548 A1* | 4/2011 | Budiman ................ G16Z 99/00 |
| | | 600/365 |
| 2013/0116649 A1 | 5/2013 | Breton et al. |
| 2014/0024907 A1 | 1/2014 | Howell et al. |
| 2014/0030748 A1 | 1/2014 | Schaible |
| 2014/0081103 A1 | 3/2014 | Schaible |
| 2014/0083867 A1 | 3/2014 | Schaible |
| 2014/0180240 A1 | 6/2014 | Finan et al. |
| 2015/0157792 A1 | 6/2015 | Chovanda et al. |
| 2015/0165120 A1 | 6/2015 | Shadforth et al. |
| 2016/0038673 A1 | 2/2016 | Morales |
| 2016/0082187 A1 | 3/2016 | Schaible et al. |
| 2016/0101232 A1 | 4/2016 | Kamath et al. |
| 2017/0189614 A1 | 7/2017 | Mazlish et al. |
| 2017/0203037 A1 | 7/2017 | Desborough et al. |
| 2018/0226150 A1* | 8/2018 | Hayter ................ A61B 5/0031 |
| 2018/0364262 A1 | 12/2018 | Malka et al. |
| 2019/0043620 A1 | 2/2019 | Patek et al. |
| 2019/0239745 A1* | 8/2019 | Koehler ................ A61B 5/743 |
| 2022/0384007 A1* | 12/2022 | Simpson ................ A61B 5/1112 |
| 2023/0263434 A1* | 8/2023 | Johnson ................ G16H 50/30 |
| | | 600/301 |
| 2023/0389844 A1* | 12/2023 | Johnson ................ G16H 50/20 |

OTHER PUBLICATIONS

Office Action (Communication) issued on Apr. 12, 2023, by the European Patent Office in corresponding European Patent Application No. 17 706 022.5. (14 pages).

* cited by examiner

METHOD, SYSTEM, AND COMPUTER READABLE MEDIUM FOR VIRTUALIZATION OF A CONTINUOUS GLUCOSE MONITORING TRACE

RELATED APPLICATION

This application claims the priority benefit of U.S. Provisional Application No. 62/288,468, filed Jan. 29, 2016, for "Method, System, and Computer Readable Medium for Virtualization of a Continuous Glucose Monitoring Trace" by Stephen D. Patek et al., the entirety of which is incorporated by reference.

STATEMENT REGARDING FEDERALLY SPONSORED RESEARCH OR DEVELOPMENT

This invention was made with government support under Grant No. DK051562, awarded by the National Institutes of Health. The government has certain rights in the invention.

FIELD

The present disclosure pertains to creation of a virtual Continuous Glucose Monitoring (CGM) trace from episodic blood glucose (BG) data.

BACKGROUND

Eating and exercise behaviors affect on glycemic outcomes in type 1 diabetes, yet these influences are difficult to assess in real-life settings. While existing mathematical models faithfully represent the dynamic relationships of (i) oral carbohydrate ingestion and (ii) glucose and insulin transport/action in various compartments of the body, accurate models of meal and exercise behaviors are needed to realistically capture the wide excursions of blood glucose observed in the field, and this has been a bottleneck in preclinical in silico evaluation of advanced systems including the artificial pancreas.

Maximizing the effectiveness of insulin therapy in type 1 and 2 diabetes, involves adapting it is critical to adapt to the characteristics of the individual patient. Endocrinologists have recognized the importance of inter- and intra-patient variability with regard to insulin sensitivity and other physiological traits, and this is reflected in the methods used to titrate insulin therapy parameters including carbohydrate ratios, correction factors, correction thresholds and targets, and basal insulin doses. Behavioral characteristics (e.g. eating, exercise, and self-treatment behaviors) are also important, for example, in separating the treatment of meals from the need to provide a basal insulin "baseline" that is adapted to circadian variability of insulin sensitivity throughout the day.

To attempt to adapt to this inter and intra-patient variability, physicians have used Continuous Glucose Monitoring (CGM) traces generated by models or interpolation of existing data. These CGM traces can then be used for retrospective analysis of blood glucose data to detect and mitigate patterns of hypo- or hyperglycemia risk throughout the day. Available patient information that could improve the accuracy of the model is not included in these known models used to generate CGM traces. In other situations the CGM data is incomplete so known techniques cannot be employed.

SUMMARY

A method is disclosed for virtualizing a continuous glucose monitoring trace for a patient, the method including estimating a patient continuous glucose monitoring trace for a time period using a mathematical model, obtaining patient episodic glucose data over the time period, and optimizing the estimated patient continuous glucose monitoring trace for the time period to fit the obtained patient episodic glucose data over the time period.

A system is also disclosed for virtualizing a continuous glucose monitoring trace for a patient, the system including an estimation module configured to estimate a patient continuous glucose monitoring trace for a time period using a mathematical model, a communications module configured to received patient episodic glucose data over the time period from a data source, an optimization module configured to modify the estimated patient continuous glucose monitoring trace for the period to fit the obtained patient episodic glucose data over the time period.

DETAILED DESCRIPTION

Embodiments disclosed herein produce a virtual continuous glucose monitoring (CGM) trace from episodic blood glucose (BG) data obtained from conventional glucometers such as glucose test strips and can also product a virtual CGM trace from incomplete CGM data. Embodiments described herein also improve the quality of a CGM trace by considering other data sources such as meal data, insulin delivery data, markers of physical activity, and other data relevant to the treatment of type 1 and type 2 diabetes.

Rather than simply interpolating the episodic glucose data or applying a mathematical model as is known, an aspect of an embodiment of the present disclosure estimates a CGM trace through (i) the use of a mathematical model that relates the patient's blood glucose concentration to the dynamic effect of measured physiological perturbations (e.g. meals, insulin, physical activity) and (ii) an additional metabolic signal that explains blood glucose variability that would otherwise be inconsistent with the available perturbation data. This additional metabolic signal may sometimes be termed an unknown metabolic signal.

The virtualized CGM trace described here is derived as the output of the mathematical model subject to a best estimate of the additional/unknown metabolic signal. This estimate prioritizes a close fit to the available episodic glucose data but which is also sensitive to the profile of historical measurements available throughout a period of time, or segment of time, such as the 24 hours of the day. The virtualization process described here may be enhanced by super positioning available data regarding perturbations onto the estimate, leading to more accurate representation of postprandial BG excursions, the mediating effect of insulin, and of physical activity, for example. The virtual CGM trace described here may be used in (i) retrospective analysis of episodic BG data (e.g. in detecting and mitigating patterns of hypo- or hyperglycemia risk throughout the day) and (ii) real-time applications where the current value of the virtual CGM value reflects an improved estimate of the patient's BG value based on both recent treatment-related data, historical BG values, and other available information.

This disclosure refers to the virtualization of the CGM trace but may also be described as reconstructing a CGM trace for a predefined period of time, or segment of time, using available information including BG data and other treatment-relevant data including meals, insulin delivery, and physical activity. In one embodiment a virtualized CGM trace may consider episodic samples of blood glucose for a segment of time, historical records of episodic samples of blood glucose that are not included in the segment of time, collections of other types of measurements of biosignals in the segment of time, and other values that parameterize the patient's blood glucose dynamic response.

Episodic samples of blood glucose include a variety of techniques such as glucose test strips and CGM data. If, for example, the segment of time is a 24 hour period, episodic samples of blood glucose are collected during the course of that period of time. More particularly, during a 24 hour period starting from midnight, glucose test strip data collected at 6 am, 12 pm, and 6 pm during the same 24 hour period are considered episodic samples of blood glucose. Historical records of episodic samples of blood glucose are historical patient episodic glucose data collected outside of the segment of time. Continuing the above example, during a 24 hour period starting from midnight, glucose test strip data collected two days earlier at 6 pm is considered historical patient episodic glucose data.

When historical records of episodic samples of blood glucose are considered by the described embodiments, more recent episodic samples of blood glucose data may be weighed more heavily than episodic samples of blood glucose data from the past. For example, the episodic samples of blood glucose data measured during the period of time may be most heavily weighed, while historical records of episodic samples of blood glucose data from the prior week are weighed less (e.g., 50% or more or less), and while historical records of episodic samples of blood glucose data from the prior month are weighed even less (e.g., 25% or more or less). All types of weighing of the different types of episodic samples of blood glucose are contemplated, but are not specifically enumerated here.

Other types of measurements of biosignals collected during the period of time may include meal acknowledgments, hypoglycemia treatments, insulin boluses, physical activity acknowledgment, and other patient treatment-related signals. The patient treatment-related signals considered biosignals are measured from the patient using any appropriate technique and are collected for consideration by the embodiments described herein. Values that parameterize the patient's blood glucose dynamic response may be specific to the patient and include body weight, average total daily insulin, average total daily basal insulin, glycated hemoglobin, or other marker of average glucose, and basal insulin profile or basal injection strategy.

Like the episodic samples of blood glucose described above, historical records of other types of measurements of treatment-related signals may also be considered. When historical records of other types of measurements of treatment-related signals are considered by the described embodiments, more recent other types of measurements of treatment-related signals may be weighed more heavily than other types of measurements of treatment-related signals from the past. For example, the other types of measurements of treatment-related signals measured during the period of time may be most heavily weighed, while historical records of other types of measurements of treatment-related signals from the prior week are weighed less, and while historical records of other types of measurements of treatment-related signals from the prior month are weighed even less. Other types of weighing of the other types of measurements of treatment-related signals are contemplated but not specifically enumerated here.

Mathematical Models

The process for building the virtual CGM trace for a period of time first relies on a mathematical model. The mathematical models estimate the patient absorption of insulin over the period of time. In at least some embodiments, the mathematical model used may differ depending on the patient. For example, a specific patient may have a physiology that is adequately modeled by a minimal compartmental model whereas another patient may have a physiology that is adequately modeled by transfer function models. A wide variety of dynamic blood glucose mathematical models may be used in the CGM virtualization process including minimal and maximal compartmental models, input/out models derived from standard statistical techniques, and transfer function models.

The mathematical model that describes the patient's metabolic responses to perturbations may take the following general form:

$$x_{k+1} = \mathbb{F}_\theta(x_k, \beta_k^i, \omega_k^i)$$

where $x_k$ is a vector of metabolic states including masses or concentrations of glucose in blood plasma and in various other compartments of the body, also potentially including masses or concentrations of insulin in various compartments, masses or concentrations of other hormones in various compartments, digestive states related to eating behavior, etcetera. The subscript k refers to the k-th stage of the segment of time in question and each discrete stage corresponds to the sampling interval of the CGM being virtualized.

$\mathbb{F}_e$ is the function that describes the evolution of metabolic states over discrete stages of time $\beta_k^i$ is the vector of biosignal inputs (meals, insulin delivery, physical activity) in the k-th stage of the i-th segment of time $\omega_k^i$ is the vector of unknown metabolic values that apply in the k-th stage of the i-th segment of time.

The virtual CGM trace for the i-th segment of time, vCGM$^i$, is derived as $$vCGM^i = \mathbb{G}_\theta(x_0^{i,*}, \beta^i, \omega^{i,*})$$

where $x_0^{i,*}$ and $\omega^{i,*}$ are respectively the best estimates of the patients dynamic initial condition at the beginning of the i-th segment and the unknown metabolic signal that explains BG excursions that would not be explained by the mathematical model $\mathbb{G}_\theta$ is function that reproduces the virtual CGM values that would be observed given the patients dynamic initial condition, the biosignals contained in $\beta^i$ that describe meals, insulin delivery, physical activity, and other treatment-relevant inputs, and the unknown metabolic signal.

Here, $x_0^{i,*}$ and $\omega^{i,*}$ are derived from the solution to an optimization problem:

$$(x_0^{i,*}, \omega^{i,*}) = \underset{(x_0,\omega)}{\text{Arg min}}\, J(BG^i, BG^{-i}, \beta^i, \omega)$$

subject to $$x_{k+1} = \mathbb{F}_\theta(x_k, \beta_k^i, \omega_k^i)$$

where J is a cost function that penalizes:
deviations in the virtualized CGM trace away from the episodic samples of blood glucose in the i-th segment of time represented in $BG^i$
deviations in the virtualized CGM trace away from historical samples of BG at corresponding times of the day in all other segments of time represented in $BG^{-i}$
deviations in the estimate of the dynamic initial condition $x_0$ away from either steady state metabolic state values or normal metabolic state values
deviations in the estimate of the unknown metabolic signal $\omega$ away from steady state or normal values
large rates-of-change in the estimate of the unknown metabolic signal $\omega$.

Compartment models may be based on the Bergman minimal model, for example. The Bergman minimal model is described in the publications such as Bergman, R. N., Ider, Y. Z., Bowden, C., Cobelli, C. (1979) "Quantitative estimation of insulin sensitivity" *Am. J. Physiol.* 236, E667-E677, the entirety of which is incorporated by reference. Bergman minimal models use a minimal number of compartments to describe the dynamic relationship between plasma glucose concentration and both glucose rate of appearance from the gut and plasma insulin concentration. Bergman minimal models may be augmented in a minimal way to account for factors such as oral carbohydrates, insulin and glucose transfer between blood plasma and interstitial tissues. Such augmentation is described in publications such as Patek, S. D., Lv, D., Ortiz, E. A., Hughes-Karvetski, C., Kulkarni, S., Zhang, Q., and Breton, M. (2016) "Empirical representation of blood glucose variability in a compartmental model" In H. Kirchsteiger et al. (eds.), *Prediction Methods for Blood Glucose Concentration, chapter* 8, Springer Lecture Notes in Bioengineering, the entirety of which is incorporated by reference. Bergman minimal models can also capture the nonlinearity of glucose-insulin interactions through a logarithmic coordinate transformation. This is demonstrated in publications such as Patek, S. D., Breton, M. D., Vereshchetin, P., Jiang, B., Kovatchev, B. (2014) "Model-Based Control of Type 1 Diabetes in 'Risk Space'", *Proc. 19th IFAC World Congress*, pp. 237-242, the entirety of which is incorporated by reference.

Maximal compartment models, in contrast, provide a detailed account of oral consumption of carbohydrates as described in publications such as Dalla Man, C., Rizza, R. A., Cobelli, C. (2007) "Meal simulation model of the glucose-insulin system," *IEEE Trans Biomedical Eng*, vol. 54, no. 10, pp. 1740-1749, the entirety of which is incorporated by reference. A detailed account of interactions with other regulatory hormones and/or physical activity may also be provided, as described in publications such as Sorensen, J. T. (1985) "A physiologic model of glucose metabolism in man and its use to design and assess improved insulin therapies for diabetes," Ph.D. dissertation, Dept. Chemical Eng., Massachusetts Inst. Technology, the entirety of which is incorporated by reference.

Input/output models derived from standard statistical techniques may be employed. The standard statistical techniques include autoregressive moving average models. Transfer function models may also be employed as described in Percival, M. W., Bevier, W. C., Wang, Y., Dassau, E., Zisser, H. C., Jovanovic, L., Doyle, F. J. (2010). "Modeling the Effects of Subcutaneous Insulin Administration and Carbohydrate Consumption on Blood Glucose. Journal of Diabetes Science and Technology," 4(5), 1214-1228, the entirety of which is incorporated by reference.

When the mathematical model being used takes the form of a set of nonlinear continuous time differential equations, the model can be linearized and discretized by standard mathematical techniques to obtain an approximate model that significantly reduces complexity when implementing the model in computer technology. For example, the model may be linearized and discretized to the following:

$$vCGM^i = \mathbb{G}_\theta(x_0^{i,*}, \beta^i, \omega^{i,*})$$

where
$x_0^{i,*}$ and $\omega^{i,*}$ are respectively the best estimates of the patients dynamic initial condition at the beginning of the segment of time and the additional/unknown metabolic signal that explains BG excursions that would not be explained by the mathematical model
$\mathbb{G}_\theta$ is function that reproduces the virtual CGM values that would be observed given the patients dynamic initial condition, the biosignals contained in $\beta^i$ that describe meals, insulin delivery, physical activity, and other treatment-relevant inputs, and the unknown metabolic signal.

Here, $x_0^{i,*}$ and $\omega^{i,*}$ are derived from the solution to an optimization problem:

$$(x_0^{i,*}, \omega^{i,*}) = \underset{(x_0,\omega)}{\text{Arg min}}\, J(BG^i, BG^{-i}, \beta^i, \omega)$$

subject to $$x_{k+1} = \mathbb{F}_\theta(x_k, \beta_k^i, \omega_k^i)$$

where J is a cost function that penalizes:
deviations in the virtualized CGM trace away from the episodic samples of blood glucose in the segment of time represented in $BG^i$
deviations in the virtualized CGM trace away from historical samples of BG at corresponding times of the day in all other segments of time represented in $BG^{-i}$
deviations in the estimate of the dynamic initial condition $x_0$ away from either steady state metabolic state values or normal metabolic state values
deviations in the estimate of the additional/unknown metabolic signal $\omega$ away from steady state or normal values
large rates-of-change in the estimate of the unknown metabolic signal $\omega$.

Segments of Time for Mathematical Models

The segments of time over which the virtual CGM is produced by embodiments described herein can be of a period of any interval length. For example, when used in retrospective applications such as the optimization of self-monitored blood glucose (SMBG) treatment, the goal may be to produce a virtual CGM trace for each 24 hour period for a larger multi-day data collection interval. Examples of parameters that are defined over 24 hour periods include basal rate, correction factor, and carbohydrate ratio profiles.

In real time applications, the virtual CGM trace is produced for a segment of time ending at the current time and would extend back in time for a specified interval such as the past 24 hours.

Any interval length of time may be employed such as 6, 8, or 12 hours, or greater or lesser. The chosen interval length of time may correspond to timeframes over which clinically relevant events occur.

At times, information outside of the segments of time may be considered to minimize edge effects. When accurate reconstruction of the continuous virtual CGM trace is desired, prepending and appending data to the beginning and end of the segment may be performed. This provides a warm-up interval before the beginning of the virtualized segment and a post interval after the end of the virtualized segment. When the segments of time are 24 hour days and prepending and appending to pad the data and reduce edge effects is desired, the resulting data segments are referred to as extended days of the historical record.

Biosignals that Inform the Virtual CGM Trace

Virtual CGM traces can be produced based on alternative sets of available biosignals including episodic BG data, meal delivery data, hypoglycemia treatment, insulin delivery data, physical activity data, and other treatment-relevant data. Each biosignal is relevant to the segment of time for which the virtual CGM trace is being generated. For example, the insulin delivery data may take the form of a dose of insulin provided by an insulin pump in the last 24 hours when the virtual CGM trace is being produced for the last 24 hours. The different types of available biosignals may be weighed differently depending on the patient, the mathematical models employed, and other factors. For example, meal delivery data may be weighed more heavily than physical activity data for a specific patient.

Although described above as being signals relevant to the segment of time for which the virtual CGM trace is being generated, in some embodiments, biosignals from outside the segment of time for which the virtual CGM trace is being generated may also be considered. For example, historical meal delivery data and physical activity data for a specific patient may be considered to further improve the virtual CGM trace generated by embodiments described herein. Similar to the biosignals described above, the different types of available historical biosignals may be weighed differently depending on the patient, the mathematical models employed, and other factors. Regarding historical biosignals, older biosignals may be weighed less than more recent biosignals, for example.

The Additive/Unknown Metabolic Signal

The additive/unknown metabolic signal that is estimated in the CGM virtualization processes can be considered an input, disturbance, or forcing function to the mathematical models described above and can be inserted at different, selectively chosen and desired, points in the mathematical model. For example, the additive/unknown signal may be modeled as an additive noise process at the site of glucose rate of appearance into blood plasma; modeled as an additive noise process at the site of oral ingestion of carbohydrates' and/or modeled at sites related to perceived insulin sensitivity such as an additive or multiplicative perturbation at the site of endogenous glucose production, and/or an additive or multiplicative perturbation at the site of insulin-dependent glucose uptake.

Objective Function Used to Determine the Best Estimate of the Additive/Unknown Metabolic Signal Embodiments disclosed herein explicitly or implicitly involve the assessment of the virtual CGM signal as a function of the state trajectory obtained from the dynamic initial condition and the additive/unknown metabolic signal along with the biosignals inputs. Embodiments may derive from the specific objective function J used to define the notion of "best fit" for the dynamic initial condition $x_0^i$ and the additive/unknown metabolic signal $\omega^i$.

For notational convenience let $y^i=(y_0^i, y_1^i, \ldots, y_T^i)'$ denote the virtual CGM signal associated with $x_0^i$ and $\omega^i$. The objective function can then be expressed in terms of:
- the distance between (i) specific samples of blood glucose in $BG^i$, for example, a sample $BG_k^i$ obtained in the k-th stage of the i-th segment of time and (ii) the corresponding virtual CGM value $y_k^i$
- the distance between (i) specific samples of blood glucose in $BG^{-i}$, for example, a sample $BG_k^{-i}$ obtained in the k-th stage of the i-th segment of time and (ii) the corresponding virtual CGM value $y_k^i$
- the magnitude of individual states values in the estimated dynamic initial condition $x_0^i$
- the magnitude of the value of the estimated unknown metabolic signal at any stage of the process $\omega_k^i$
- the rate of change (one-step or multi-step differences) of the unknown metabolic signal, e.g. $\{(\omega_1^i-\omega_0^i), (\omega_2^i-\omega_1^i), \ldots, (\omega_T^i-\omega_{T-1}^i),\}$ Other embodiments derive from the specific functional form of the cost function, including objective functions that are quadratic in all error rates with weighing parameters on different classes of terms reflecting the relative importance. For example, when producing the virtual CGM trace, it may be desirable to heavily weight the errors associated with BG samples in $BG^i$ and less heavily weight errors associated with BG samples in $BG^{-i}$.

Still further embodiments derive from the specified functional form of the cost function where the objective functions are quadratic in $y^i$ and $x_0^i$ but penalize the linear magnitude of the additive/unknown metabolic signal, where the objective functions involve cross terms associated with the different classes of error terms above, and where the objective functions have polynomial degrees greater than two, or non-polynomial structure.

EXAMPLE EMBODIMENT

Figure 1A:
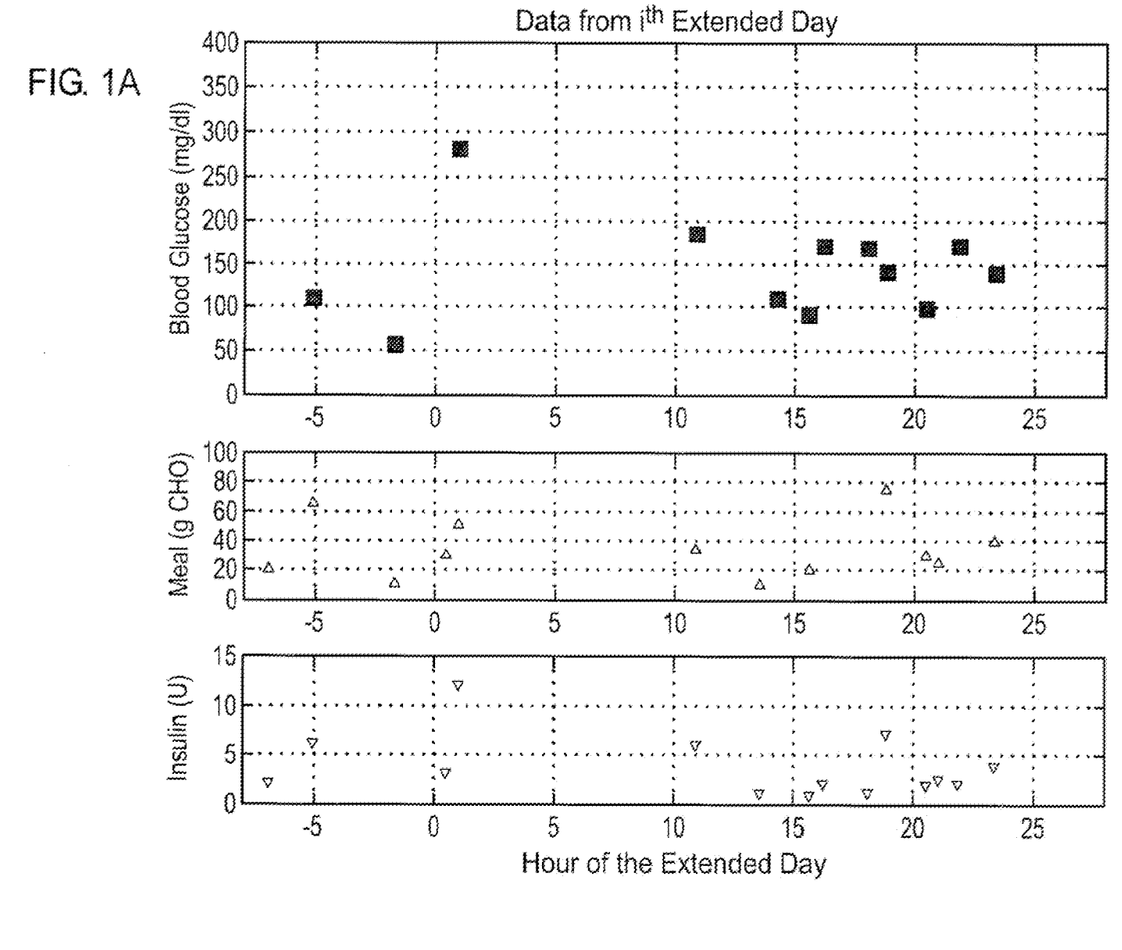
FIGS. 1A-1C depict an aspect of the output from an exemplary disclosed embodiment.
Figure 1B:
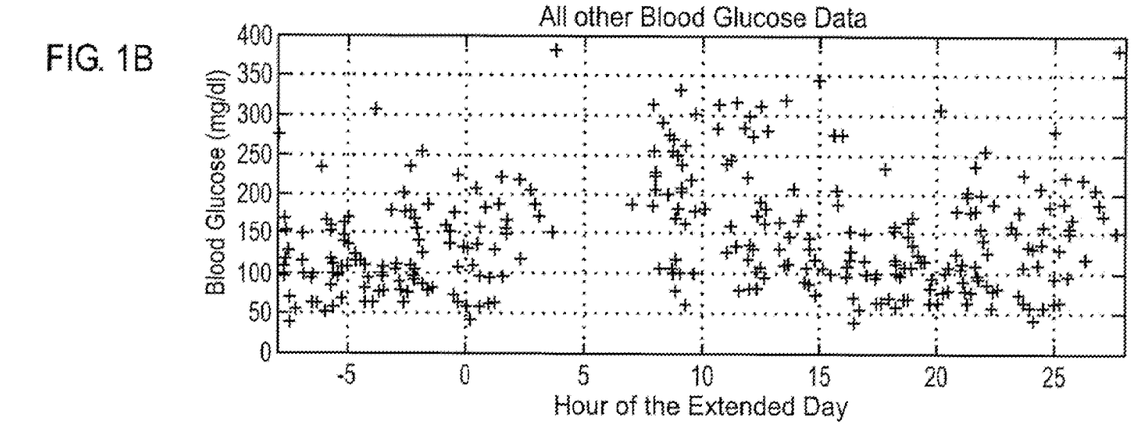
Figure 1C:
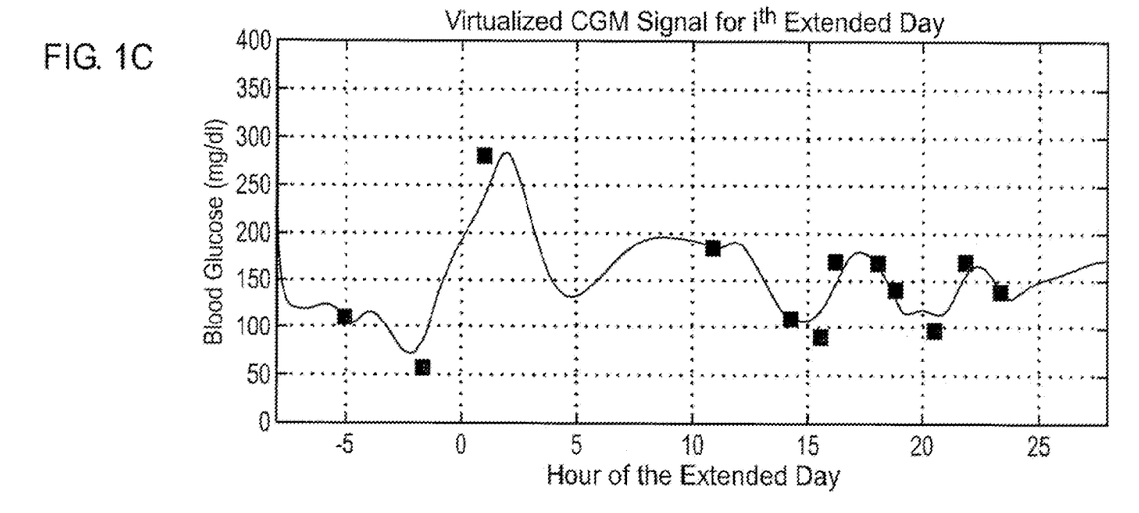

FIGS. 1A-1C illustrate a manifestation of an aspect of an embodiment disclosed here where:
- (AM.1) virtual CGM traces are obtained for 36-hour "extended days" within a data set of SMBG values
- (AM.2) the available biosignals in the dataset are meal, and insulin bolus values, with each "extended day" starting eight hours before midnight and ending four hours after the following midnight
- (AM.3) a subcutaneous oral glucose minimal model is used to describe the dynamic relationship between (i) plasma glucose concentration and (ii) meal and insulin inputs, where the model is linearized about the average BG value associated with the patient's HbA1c and average rate of basal insulin delivery
- (AM.4) the unknown metabolic signal enters the model at the point of glucose rate of appearance
- (AM.5) the objective function quadratic in all error terms $(BG_k^i-y_k^i)$ and $(BG_k^{-i}-y_k^i)$, initial condition values $x_0^i$, unknown metabolic inputs $\omega_k^i$, and one-step differences $(\omega_k^i-\omega_{k-1}^i)$.

The red continuous trace shown in the plot on the right is the virtual CGM trace associated with (i) the BG and biosignal data associated with the i-th extended day, i.e. $BG^i$ and $\beta^i$ and (ii) all of the other historical BG values $BG^{-i}$.

Note that the red trace exhibits significantly more variability than would be obtained in simply "connecting" the BG samples with straight lines. For example, the dramatic drop in BG after midnight (hour zero) is consistent with the large insulin bolus taken just prior to first BG sample after midnight.

Certain advantages are provided by the embodiments described herein. For example, the disclosed embodiments provide, among other things, a means of extrapolating or smoothing episodic BG measurements to obtain a continuous estimate of BG between data samples. Rather than simply numerically interpolating the values (e.g. with a cubic spline) as has been done, the virtual CGM trace produced here (i) corresponds to the output of a mathematical model of the patient's blood glucose dynamic system, (ii) exhibits artifacts that are consistent with other available information (e.g. postprandial glucose excursions, effects of insulin actions, effects of physical activity), and (iii) is influenced by the historical record of all BG measurements. Additionally, gaps in the BG record on a particular day are corrected by the availability BG measurements in the gap interval on other days in the historical record.

Another example is the ability to reconstruct a virtual CGM trace from a record of episodic BG measurements to create a bridge to analytic methods that require CGM as the primary glucose input, including (i) retrospective adaptive advisory systems (e.g. systems for retrospective treatment optimization) and (ii) real-time treatment advisory systems. For example, an aspect of an embodiment helps enable the application of the technique in U.S. patent application Ser. No. 14/241,383 to situations where only SMBG values are available.

An aspect of various embodiments may be utilized for a number of products and services. For example, virtual CGM traces can be used in any retrospective or real-time application that requires CGM as an input and where only episodic BG data are available. An aspect of various embodiments may also be utilized in CGM virtualization in: (i) retrospective systems risk profiling, insulin sensitivity profiling, and treatment optimization where the only available BG measurements are episodic (e.g. "fingerstick" SMBG values) and (ii) in systems for real-time treatment advice (e.g. bolus or exercise advice) where CGM virtualization provides the best estimate of current or recent continuous BG based on available episodic measurements. More broadly, the described embodiments may be applicable to other metabolic processes where gaps in the collected data have previously prevented analysis and treatment regimes. Further, the applications identified above would fit within a cloud analytic framework, whereas the real-time applications may take form as a hybrid of cloud and embedded computation.

Figure 2:
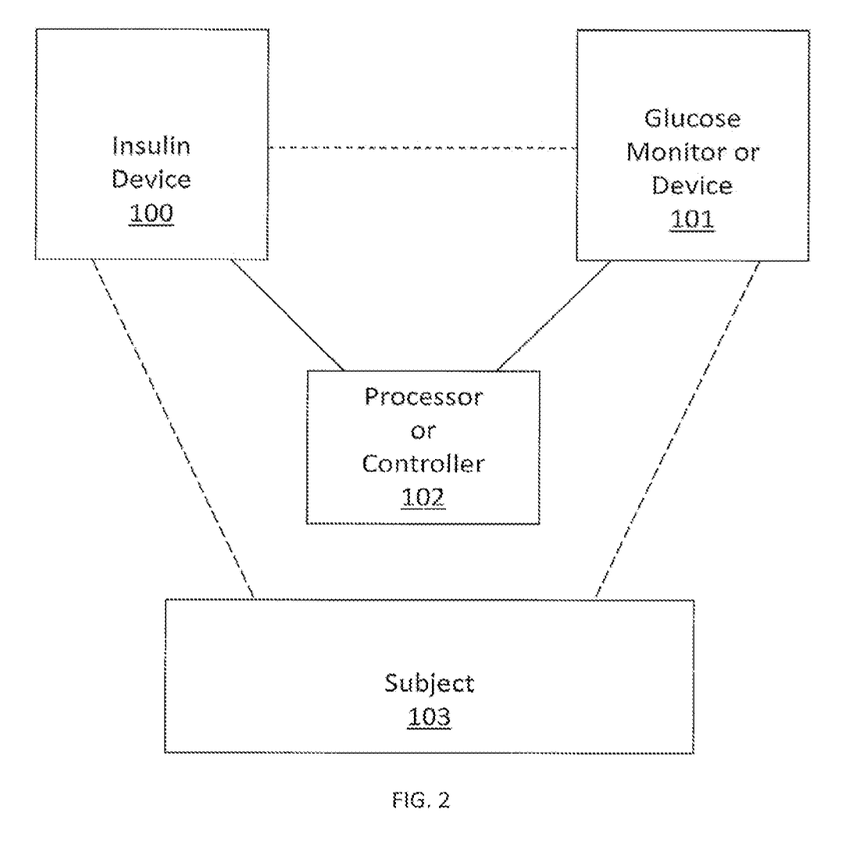
FIG. 2 depicts a high level functional block diagram of an exemplary embodiment.

FIG. 2 is a high level functional block diagram of an embodiment, or an aspect of such an embodiment.

As shown in FIG. 2, a processor or controller 102 communicates with the glucose monitor or device 101, and optionally the insulin device 100. The glucose monitor or device 101 communicates with the subject 103 to monitor glucose levels of the subject 103. The processor or controller 102 is configured to perform any specified and/or required calculations. Optionally, the insulin device 100 communicates with the subject 103 to deliver insulin to the subject 103. The processor or controller 102 is configured to perform the required calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device.

Figure 3A:
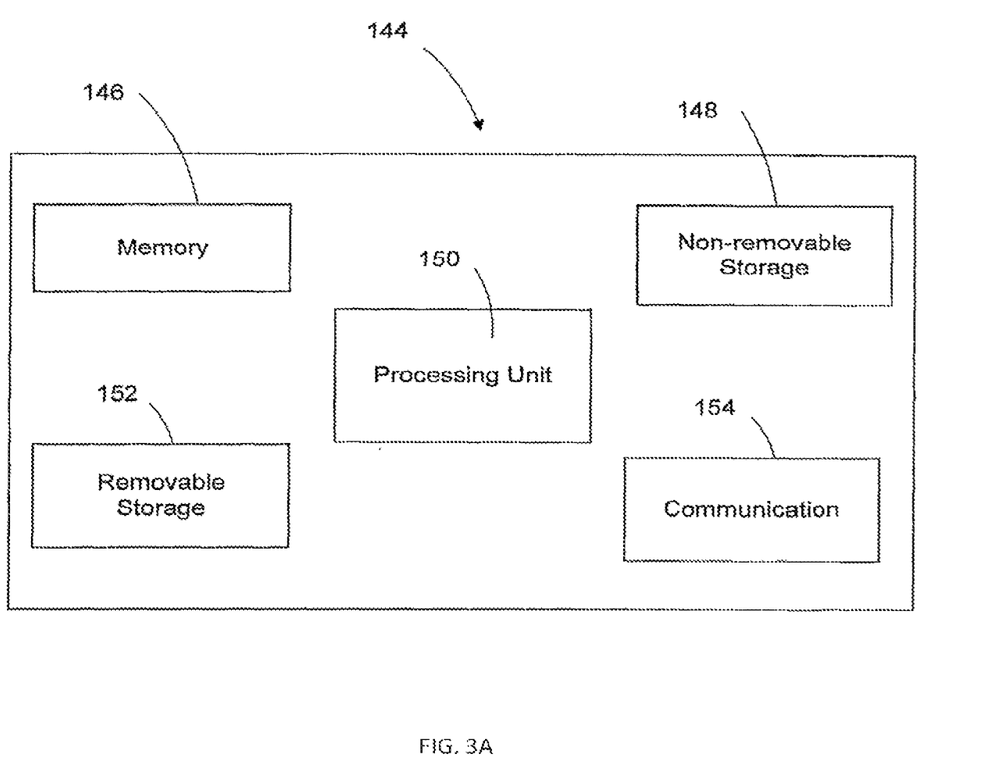
FIG. 3A depicts an exemplary computing device.

Referring to FIG. 3A, in its most basic configuration, computing device 144 can include at least one processing unit 150 and memory 146. Depending on the exact configuration and type of computing device, memory 146 can be volatile (e.g. RAM), non-volatile (e.g. ROM, flash memory, etc.) or some combination of the two.

Additionally, device 144 may also have other features and/or functionality. For example, the device could also include additional removable and/or non-removable storage including magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage, and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media can embody computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 3B:
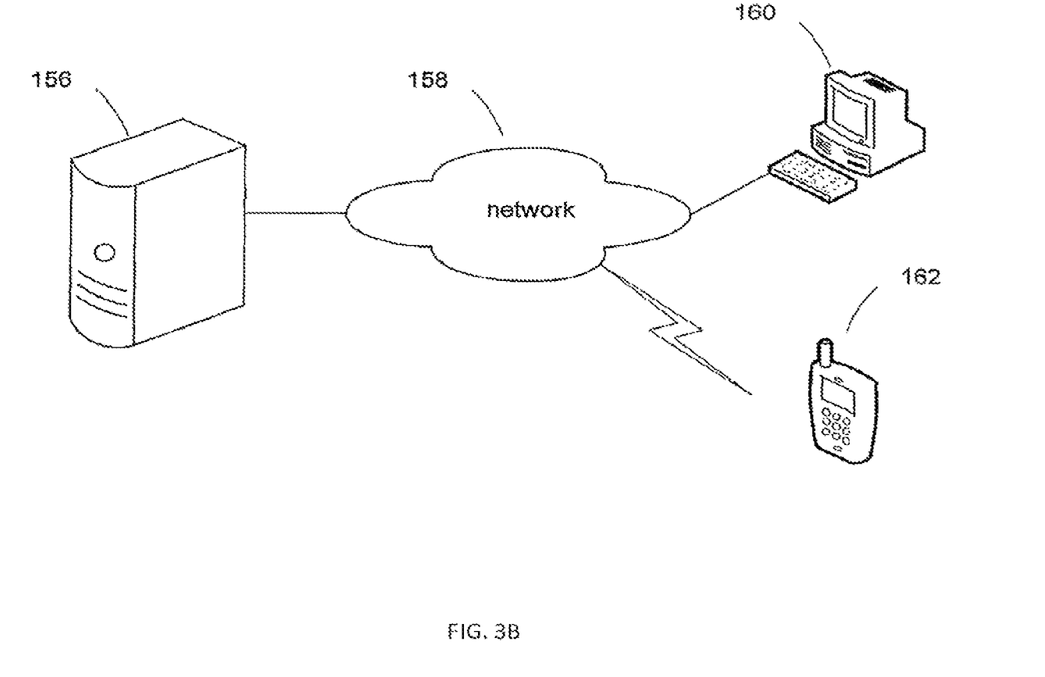
FIG. 3B depicts an exemplar network system.

In addition to a stand-alone computing machine, exemplary embodiments can also be implemented on a network system comprising a plurality of computing devices that are in communication with a networking means, such as a network with an infrastructure or an ad hoc network. The network connection can be wired connections or wireless connections. As a way of example, FIG. 3B illustrates a network system in which disclosed embodiments can be implemented. In this example, the network system comprises computer 156 (e.g. a network server), network connection means 158 (e.g. wired and/or wireless connections), computer terminal 160, and PDA 162 (e.g. a smart-phone, cell phone, laptop computer, tablet computer, GPS receiver, mp3 player, handheld video player, pocket projector, handheld devices, or non-portable devices with combinations of such features). In an embodiment, it should be appreciated that the module listed as 156 may be glucose monitor device. In an embodiment, it should be appreciated that the module listed as 156 may be a glucose monitor device (or glucose meter) and/or an insulin device. Any of the components shown or discussed with FIG. 3B may be multiple in number.

The disclosed embodiments can be implemented in anyone of the devices of the system. For example, execution of the instructions or other desired processing can be performed on the same computing device that is anyone of 156, 160, and 162. Alternatively, an embodiment can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa.

Certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 or an access point in an ad hoc network. For another example, software to be protected can be executed, encoded, or processed with one or more embodiments of the invention. The processed, encoded, or executed software can then be distributed to customers. The distribution can be in a form of storage media (e.g. disk) or electronic copy.

Figure 4:
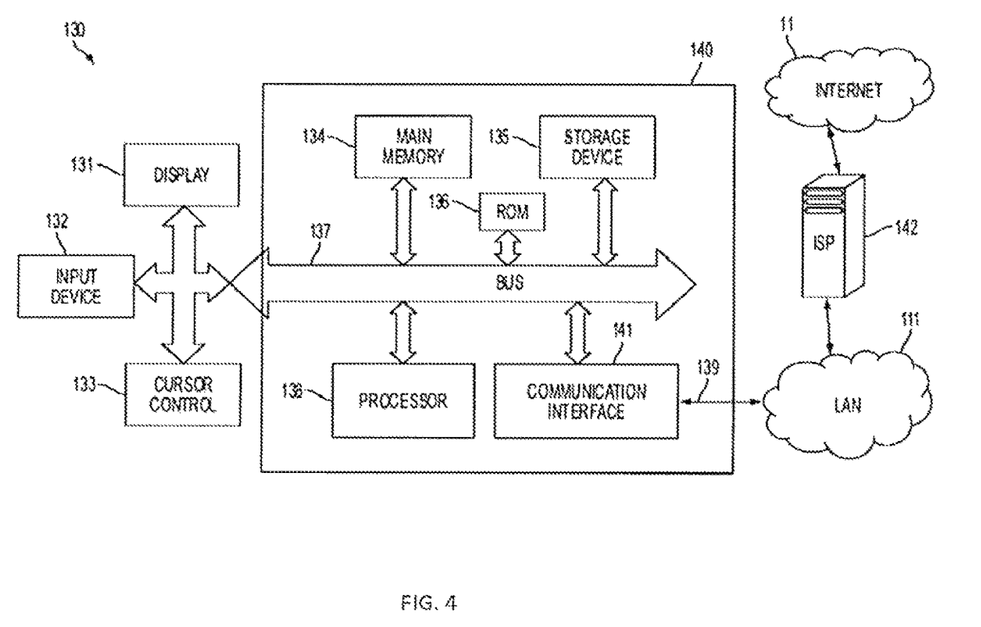
FIG. 4 depicts a block diagram of an exemplary system.

FIG. 4 is a block diagram that illustrates a system 130 including a computer system 140 and the associated Internet 11 connection upon which an embodiment may be implemented. Such configuration can be used for computers connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 4. The system 140 may be used as a portable electronic device such as a notebook/laptop computer, a media player (e.g. MP3 based or video player), a cellular phone, a Personal Digital Assistant (PDA), a glucose monitor device, an insulin delivery device, an image processing device (e.g. a digital camera or video recorder), and/or any other handheld computing devices, or a combination of any of these devices.

Note that while FIG. 4 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system of FIG. 4 may, for example, be an Apple Macintosh computer, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (e.g. DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Computer system 140 can include an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g. silicon die), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor, or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device can have two degrees of freedom in two axes, a first axis (e.g. x) and a second axis (e.g. y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, disclosed embodiments are not limited to any specific combination of hardware circuitry and software.

The term "computer-readable medium" (or "machine-readable medium") as used herein is an extensible term that refers to any medium or any memory, that participates in providing instructions to a processor, such as processor 138, for execution, or any mechanism for storing or transmitting information in a form readable by a machine (e.g. a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire, and fiber optics, including the wires that comprise bus 137. Transmission media can also take the form of acoustic or light waves, such as those generated during radio-wave and infrared data communications, or other form of propagated signals (e.g. carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (June 2099), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (Feb. 20, 2004), which is incorporated in its entirety.

Wireless links may also be implemented. In any such implementation, communication interface 141 sends and receives electrical, electromagnetic, or optical signals that carry digital data streams representing various types of information.

Network link 139 can provide data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic, or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concept of virtualization of a continuous glucose monitoring trace from recent and historical episodic blood glucose measurements and other available biosignals—have been developed and disclosed herein; and may be implemented and utilized with the related processors, networks, computer systems, internet, and components and functions according to the schemes disclosed herein.

Figure 5:
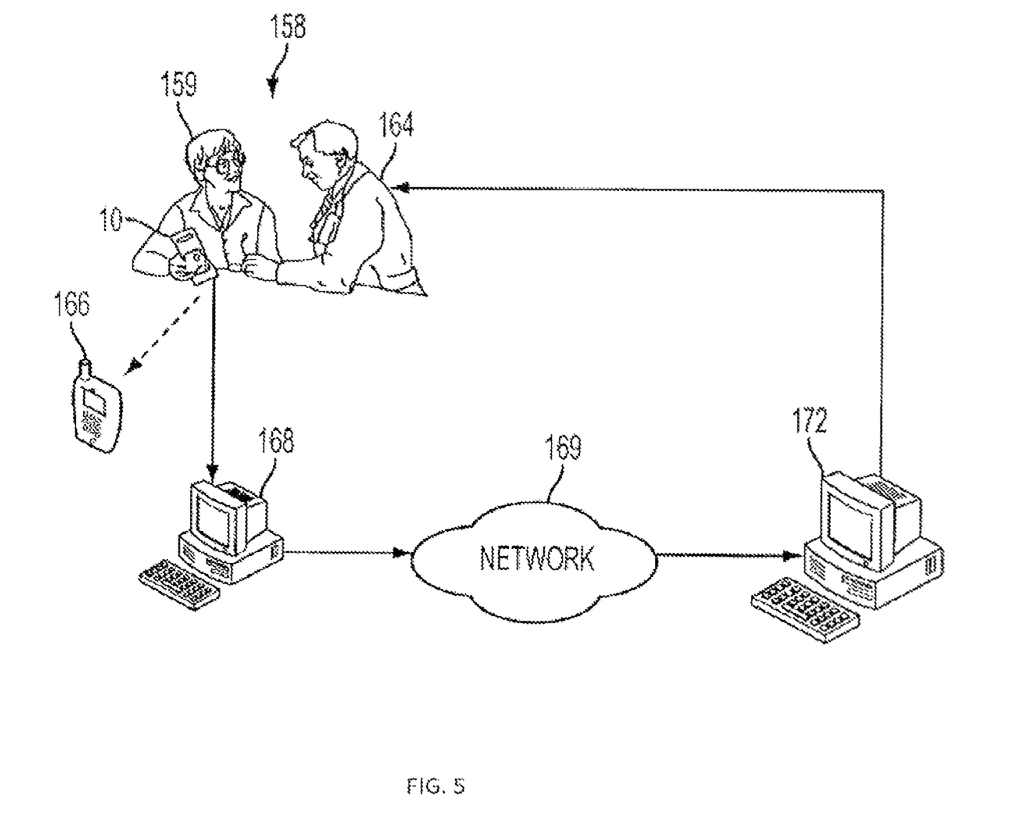
FIG. 5 depicts an exemplary system.

FIG. 5 illustrates a system in which one or more embodiments disclosed herein can be implemented using a network, or portions of a network or computers. Although the disclosed glucose device may be practiced without a network.

FIG. 5 diagrammatically illustrates an exemplary system in which examples of the invention can be implemented. In an embodiment the glucose monitor or glucose meter (and/or insulin pump) may be implemented by the subject (or patient) locally at home or other desired location. However, in an alternative embodiment it may be implemented in a clinic setting or assistance setting. For instance, referring to FIG. 5, a clinic setup 158 provides a place for doctors 164 or clinician/assistant to diagnose patients 159 with diseases related with glucose and related diseases and conditions. A glucose monitoring device 10 can be used to monitor and/or test the glucose levels of the patient—as a standalone device. It should be appreciated that while only glucose monitor device 10 is shown in the figure, the system disclosed herein and any component thereof may be used in the manner depicted by FIG. 5. The system or component may be affixed to the patient or in communication with the patient as desired or required. For example the system or combination of components thereof—including a glucose monitor device 10 (or other related devices or systems such as a controller, and/or an insulin pump, or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions or modeling. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring, modeling and/or accuracy enhancement for glucose centers, due to the importance of the glucose sensors.

Examples disclosed herein can also be implemented in a standalone computing device associated with the target glucose monitoring device. An exemplary computing device (or portions thereof) in which examples of the invention can be implemented is schematically illustrated in FIG. 3A.

Figure 6:
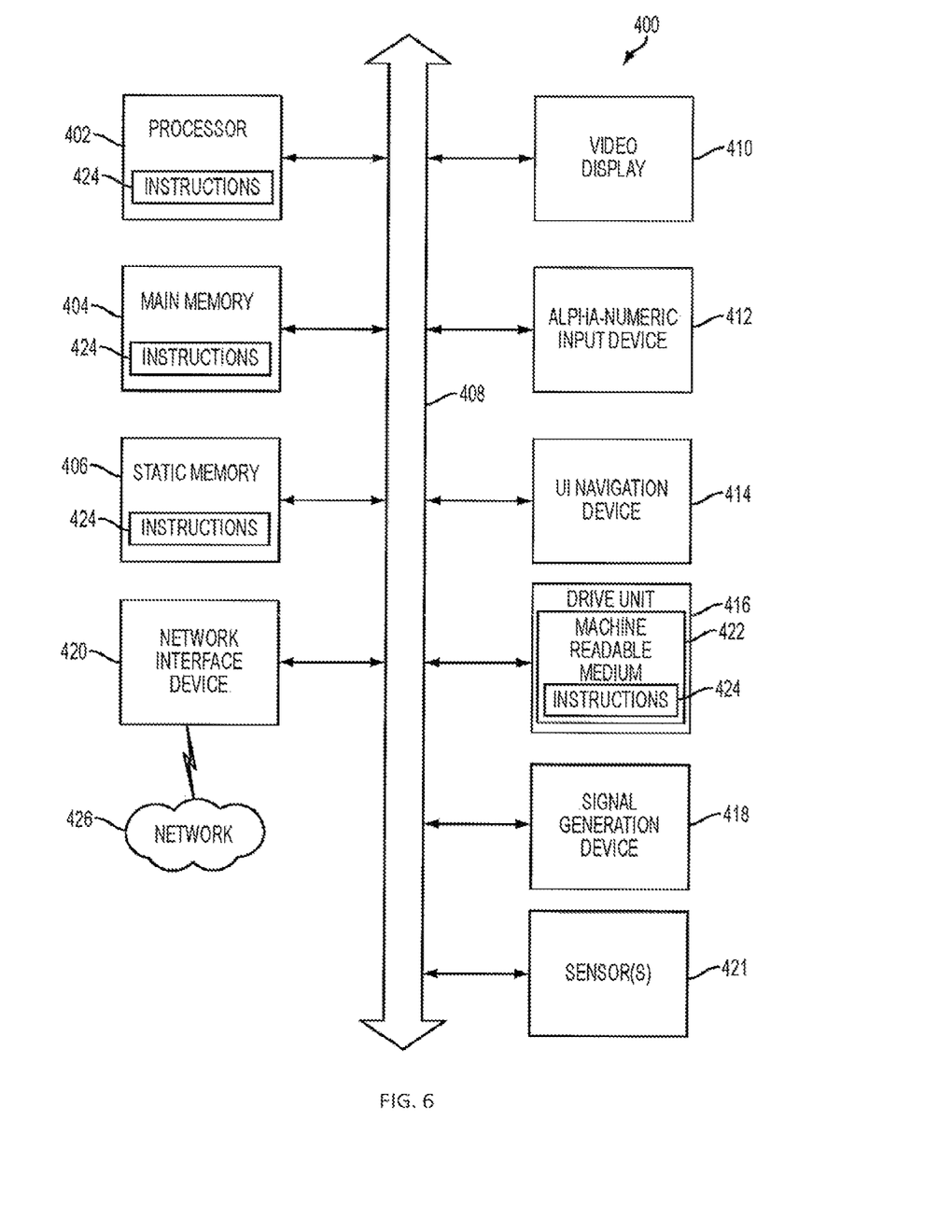
FIG. 6 depicts a block diagram of an exemplary machine.

FIG. 6 is a block diagram illustrating an example of a machine upon which one or more aspects of embodiments of the present invention can be implemented.

FIG. 6 illustrates a block diagram of an example machine 400 upon which one or more embodiments (e.g. discussed methodologies) can be implemented (e.g. run).

Examples of machine 400 can include logic, one or more components, circuits (e.g. modules), or mechanisms. Circuits are tangible entities configured to perform certain operations. In an example, circuits can be arranged (e.g. internally or with respect to external entities such as other circuits) in a specified manner. In an example, one or more computer systems (e.g. a standalone, client or server computer system) or one or more hardware processors (processors) can be configured by software (e.g. instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g. circuitry, as encompassed within a general-purpose processor or other programmable processor) that can be temporarily configured (e.g. by software) to perform the certain operations. It will be appreciated that the decision to implement a circuit mechanically (e.g. in dedicated and permanently configured circuitry), or in temporarily configured circuitry (e.g. configured by software) can be driven by cost and time considerations.

Accordingly, the term "circuit" is understood to encompass a tangible entity, be that an entity that is physically constructed, permanently configured (e.g. hardwired), or temporarily (e.g. transitorily) configured (e.g. programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g. over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g. a collection of information).

The various operations of method examples described herein can be performed, at least partially, by one or more processors that are temporarily configured (e.g. by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g. within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers, with these operations being accessible via a network (e.g. the Internet) and via one or more appropriate interfaces (e.g. Application Program Interfaces).

Example embodiments (e.g. apparatus, systems, or methods) can be implemented in digital electronic circuitry, in computer hardware, in firmware, in software, or in any combination thereof. Example embodiments can be implemented using a computer program product (e.g. a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g. a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g. an ASIC), in temporarily configured hardware (e.g. a combination of software and a programmable processor), or a combination of permanently and temporarily configured hardware can be a design choice. Below are set out hardware (e.g. machine 400) and software architectures that can be deployed in example embodiments.

In an example, the machine 400 can operate as a stand-alone device or the machine 400 can be connected (e.g. networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g. performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g. computer system) 400 can include a processor 402 (e.g. a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g. a keyboard), and a user interface (UI) navigation device 411 (e.g., a mouse). In an example, the display unit 410, input device 412 and UI navigation device 414 can be a touch screen display. The machine 400 can additionally include a storage device (e.g. drive unit) 416, a signal generation device 418 (e.g. a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g. software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g. a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g. Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g. frame relay, IP, TCP, UDP, HTTP, etc.). Example communication networks can include a local area network (LAN), a wide area network (WAN), a packet data network (e.g. the Internet), mobile telephone networks (e.g. cellular networks), Plain Old Telephone (POTS) networks, and wireless data networks (e.g. IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

It should be appreciated that any of the components or modules referred to with regards to any of the present invention embodiments discussed herein, may be integrally or separately formed with one another. Further, redundant functions or structures of the components or modules may be implemented.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method for titrating insulin therapy for a patient, the method comprising:
   estimating, via an estimation module, a patient continuous glucose monitoring trace for a time period using a mathematical model, the mathematical model including a parameter that is representative of an estimated metabolic signal related to blood glucose excursions unexplained by the mathematical model, wherein the estimating includes inserting at one or more selected points: an additive noise process at a site of glucose rate of appearance into blood plasma, an additive noise process at a site of oral ingestion of carbohydrates, or an additive noise process modeled at a site related to perceived insulin sensitivity, the site related to perceived insulin sensitivity including an additive or multiplicative perturbation at a site of endogenous glucose production and/or an additive or multiplicative perturbation at a site of insulin-dependent glucose uptake;
   obtaining, via a communication module, patient glucose data at least partially before the time period and at least partially over the time period;
   modifying, via an optimization module, the estimated patient continuous glucose monitoring trace for the time period to fit the obtained patient glucose data over the time period using a cost function that penalizes one or more of:
   deviations of the estimated continuous glucose monitoring trace away from blood glucose samples, if any, of the glucose data obtained before and/or during the time period; and
   a rate-of-change in the estimated metabolic signal that is greater than a pre-determined rate-of-change; and
   titrating, via a controller of an insulin delivery device, at least one of carbohydrate ratios, correction factors, correction thresholds, correction targets, insulin sensitivity, basal insulin rates, or basal insulin doses based on the modified estimated patient continuous glucose monitoring trace.

2. The method of claim 1, comprising:
   obtaining at least one of patient biosignals or patient factors; and
   wherein the modifying of the estimated patient continuous glucose monitoring trace further fits the obtained at least one of patient biosignals or patient factors.

3. The method of claim 2, wherein the modifying of the estimated patient continuous glucose monitoring trace uses a higher weight for recent information than less recent information.

4. The method of claim 1, wherein the estimated patient continuous glucose monitoring trace includes data collected after the time period.

5. The method of claim 1, comprising:
   obtaining patient treatment relevant data;
   wherein the modifying of the estimated patient continuous glucose monitoring trace further fits the obtained patient treatment relevant data.

6. The method of claim 1, wherein the mathematical model used to estimate the patient continuous glucose monitoring trace is individualized to the patient.

7. A system for titrating insulin therapy for a patient, the system comprising:
   an estimation module configured to estimate a patient continuous glucose monitoring trace for a time period using a mathematical model, the mathematical model including a parameter that is representative of an estimated metabolic signal related to blood glucose excursions unexplained by the mathematical model, wherein the estimating includes inserting at one or more selected points: an additive noise process at a site of glucose rate of appearance into blood plasma, an additive noise process at a site of oral ingestion of carbohydrates, or an additive noise process modeled at a site related to perceived insulin sensitivity, the site related to perceived insulin sensitivity including an additive or multiplicative perturbation at a site of endogenous glucose production and/or an additive or multiplicative perturbation at a site of insulin-dependent glucose uptake;
   a communications module configured to received patient glucose data before the time period and over the time period from a data source;
   an optimization module configured to modify the estimated patient continuous glucose monitoring trace for the time period to fit the obtained patient episodic glucose data over the time period using a cost function that penalizes one or more of:
   deviations of the estimated continuous glucose monitoring trace away from blood glucose samples, if any, of the glucose data obtained before and/or during the time period; and
   a rate-of-change in the estimated metabolic signal that is greater than a pre-determined rate-of-change; and
   an insulin delivery device controller configured to titrate at least one of carbohydrate ratios, correction factors, correction thresholds, correction targets, insulin sensitivity, basil insulin rates, or basal insulin doses based on the modified estimated patient continuous glucose monitoring trace.

8. The system of claim 7, wherein the communications module is configured to receive at least one of patient biosignals or patient factors; and
   wherein the optimization module further fits the obtained at least one of patient biosignals or patient factors.

9. The system of claim 8, wherein the optimization module uses a higher weight for recent information than less recent information.

10. The system of claim 7, wherein the estimation module includes data collected after the time period.

11. The system of claim 7, wherein the communications module is configured to receive patient treatment relevant data; and
    wherein the optimization module further fits the obtained patient treatment relevant data.

12. The system of claim 7, wherein the mathematical model used by the estimation module to estimate the patient continuous glucose monitoring trace is individualized to the patient.

* * * * *